United States Patent
Jiang et al.

(10) Patent No.: US 7,700,915 B2
(45) Date of Patent: Apr. 20, 2010

(54) METHOD, COMPUTER PROGRAM AND APPARATUS FOR THE CHARACTERIZATION OF MOLECULES

(75) Inventors: Hua Jiang, Espoo (FI); David P. Brown, Helsinki (FI); Albert G. Nasibulin, Espoo (FI); Esko I. Kauppinen, Helsinki (FI)

(73) Assignee: Canatu Oy, Espoo (FI)

( * ) Notice: Subject to any disclaimer, the term of this patent is extended or adjusted under 35 U.S.C. 154(b) by 200 days.

(21) Appl. No.: 11/604,726

(22) Filed: Nov. 28, 2006

(65) Prior Publication Data

US 2008/0121802 A1 May 29, 2008

(51) Int. Cl.
*G01N 23/00* (2006.01)
*G21K 7/00* (2006.01)

(52) U.S. Cl. .............. 250/307; 250/306; 250/310; 250/311; 977/881; 977/742; 977/750

(58) Field of Classification Search ............. 250/306, 250/307, 310, 311; 977/839, 881, 750
See application file for complete search history.

(56) References Cited

U.S. PATENT DOCUMENTS

| | | | | |
|---|---|---|---|---|
| 5,475,218 | A * | 12/1995 | Kakibayashi et al. | 250/311 |
| 6,591,658 | B1 * | 7/2003 | Yedur et al. | 977/881 |
| 6,867,862 | B2 * | 3/2005 | Nikoonahad | 356/340 |
| 7,335,882 | B1 * | 2/2008 | Brown et al. | 250/311 |
| 2002/0014589 | A1 * | 2/2002 | Daimon | 250/306 |
| 2004/0213443 | A1 * | 10/2004 | Haussecker et al. | 382/128 |
| 2006/0033037 | A1 * | 2/2006 | Kawasaki et al. | 250/492.22 |
| 2007/0023659 | A1 * | 2/2007 | Sergeevich et al. | 250/311 |
| 2008/0099677 | A1 * | 5/2008 | Yoshida | 250/311 |

OTHER PUBLICATIONS

Kociak et al. "How Accurate Can the Determination of Chiral Indices of Carbon Nanotubes Be?" European Physical Journal B, 32, 457-469 (May 7, 2003).*
Liu, Zejian, "Atomic Structure Determination of carbon nanotubes by electron diffraction," PhD Thesis, published 2005, University of North Carolina—Chapel Hill, pp. 78-94.*
Jiang et al. Robust Bessel-function-based method for determination of the (m,n,) indices of single-walled carbon nanotubes by electron diffraction. Phys. Rev. B74, 035427 (2006), the whole document, especially abstract, section III.
Gao et al. Structure determination of individual single-wall carbon nanotubes by nanoarea electron diffraction. Appl. Phys. Lett 82, 2703 (2003), the whole document.
Liu et al. Accurate determination of atomic structure of multiwalled carbon nanotubes by nondestructive nanobeam electron diffraction. Appl. Phys. Lett. 86, 191903 (2005), the whole document.

* cited by examiner

*Primary Examiner*—Jack I Berman
*Assistant Examiner*—Brooke Purinton
(74) *Attorney, Agent, or Firm*—Young & Thompson

(57) ABSTRACT

The present invention relates to a method, computer program and device for determining the crystal structure and/or the range of crystal structures of one or more crystalline tubular molecules from a set of calibration-free properties of a diffraction pattern of the one or more crystalline tubular molecules.

19 Claims, 8 Drawing Sheets

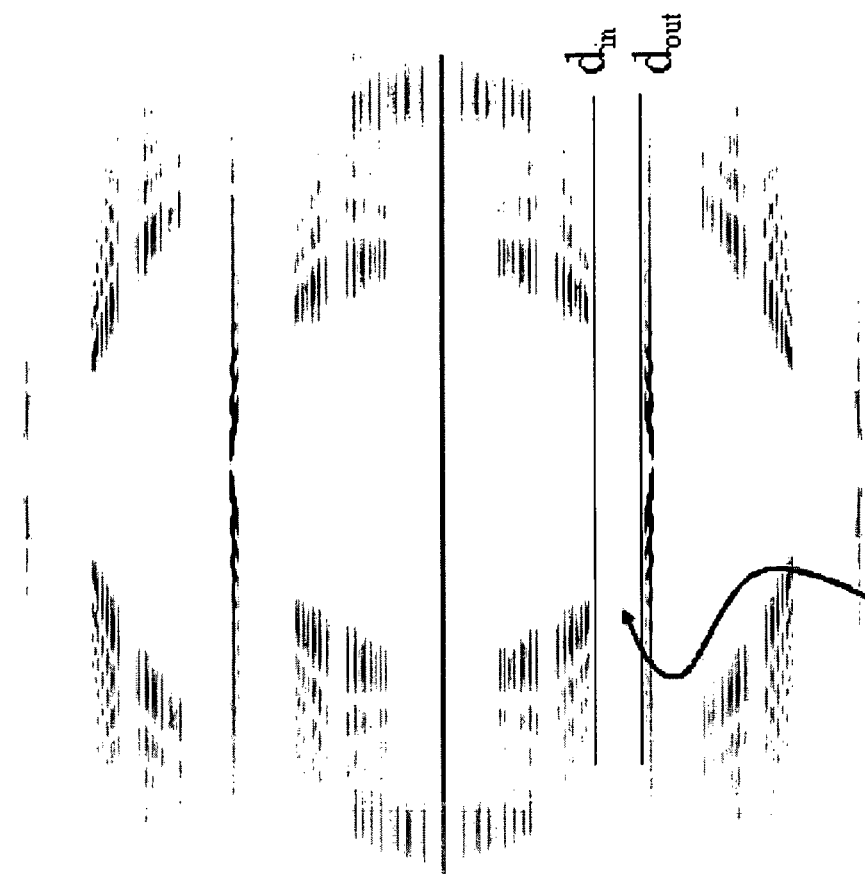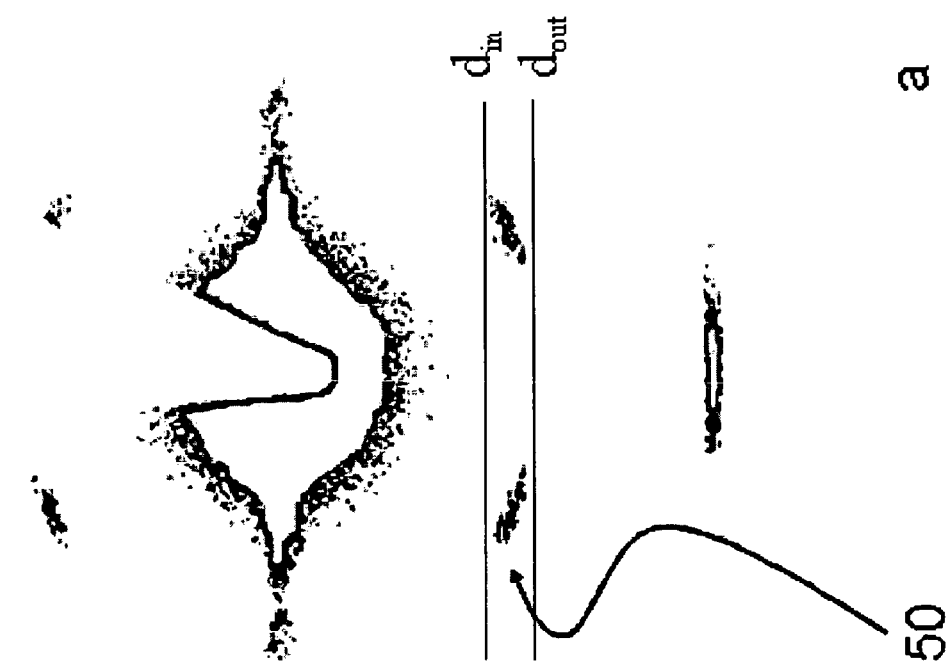
Fig. 5

METHOD, COMPUTER PROGRAM AND APPARATUS FOR THE CHARACTERIZATION OF MOLECULES

BACKGROUND OF THE INVENTION

1. Field of the Invention

The present invention relates to a method, computer program and device for determining the crystal structure and/or the range of crystal structures of one or more crystalline tubular molecules from a set of calibration-free properties of a diffraction pattern of the one or more crystalline tubular molecules.

2. Description of the Related Art

Various crystalline tubular molecules have been discovered in recent years including carbon Nanotubes and nanobuds and boron-nitride Nanotubes. Carbon Nanotubes have received the most attention because of their unique physical, chemical, thermal and electrical properties. A fundamental problem in both basic and applied research on crystalline tubular molecules such as single-walled carbon nanotubes (SWCNTs) exists because many physical properties of nanotubes can be extremely sensitive to their atomic structure. For instance, the structure of a SWCNT can be conveniently described by a pair of integers known as the chiral indices (n, m). A well-known example of the sensitivity of structure to properties is that a carbon nanotube can be metallic if (n–m) is divisible by 3, otherwise they are semiconducting. A slight change in the value n or m can, thus, dramatically alter the electronic properties of a nanotube. For instance, a (13, 1) tube is metallic while a (14, 1) tube is semiconducting though they are geometrically very similar to each other. Therefore, unambiguous (n, m) determination of individual SWCNTs is of crucial value for progressing CNT-based nanotechnology.

Current efforts for structural characterization of SWCNTs can be categorized into two broad classes, i.e., optical and non-optical. Optical spectroscopy includes, for example, resonant Raman scattering and photoluminescence, where (n, m) are identified by using the characteristic optical transition energies and photon frequencies (in Raman scattering) or optical absorption and emission energies (in photoluminescence). Optical measurements are usually limited in that they require a range of laser wavelengths for detecting a variety of tubes and they are only valid for a limited range of tube diameters. Laborious tasks are usually involved for both measurement and data interpretation. Photoluminescence has an additional drawback since the method can only detect semiconducting nanotubes. In addition, the insufficient spatial resolution of optical measurements makes it impossible to probe individual SWCNTs for analysis without considering effects from the tube environment. Moreover, there is no known calibration technique to correlate the intensity of excitations for tubes of given chiral indices to their concentrations, thus it is difficult to accurately map the chirality distribution in a SWCNT sample with optical measurements.

In the non-optical communities, the chiral indices are usually assigned by first determining the characteristic tube diameter $D_0$ and chiral angle $\alpha$ by means of direct imaging techniques in real space (e.g. scanning tunneling microscopy (STM) and high-resolution transmission electron microscopy (HRTEM)), or in reciprocal space by the electron diffraction technique. Direct imaging techniques are faced with the problem that the tubes are usually not stable enough for acquiring high-quality images with atomic-resolution and at a high magnification.

Electron diffraction was the first technique to be used to characterize SWCNTs at the time of their discovery and has remained one of the most powerful means for their structural analysis. Advanced nano-beam electron diffraction techniques uniquely allow direct probing of individual nanotubes and characterization of their structure. However, the measurements are typically made by assuming a normal incidence condition or a small tube tilting angle, e.g. less than 6°. In contrast, it is not rare for a nanotube to have a tilt angle of 20° from the horizontal plane. In practice, it is difficult to establish an experimental setup to ensure such small tilt angle requirements. Although determination of the chiral angle $\alpha$ from electron diffraction patterns (EDPs) was shown to be independent of tube inclination, evaluation of the tube diameter may rely on the tilt of the tube unless the diffraction patterns are actually calibrated by internal standard materials, which are in practice unavailable in the measurement. In the absence of such standards, absolute calibration of an EDP of a SWCNT depends on the value of the carbon-carbon (C—C) bonding distance, which has uncertainty between 0.142 nm and 0.144 nm. Additionally the C—C bond can be stretched when the tube diameter is small. Also, calibration of the EDP by using the C—C bonding distance is either tilt sensitive or complicated by the curvature of the tube. In order to take into account the tilting effect of the tube on the determination, a tedious trial-and-error simulation procedure has to be applied.

Moreover, when $D_0$ and $\alpha$ are required to be determined prior to (n, m) assignment, as by previous methods, they must both be determined with high accuracy in order to determine chiral indices n and m unambiguously. For instance, the metallic (13, 1) tube where $D_0=1.06$ nm and $\alpha=3.7°$, is very similar to the semi-conducting (14, 1) tube where $D_0=1.14$ nm and $\alpha 3.4°$. Obviously, a slight error in either $D_0$ or $\alpha$ easily leads to an ambiguity in indexing a SWCNT.

SUMMARY OF THE INVENTION

To overcome these deficiencies, we introduce a new invention: a method for determining the atomic structure of at least one tubular crystalline molecule, wherein the method comprises the following steps:

obtaining a diffraction pattern of at least one tubular crystalline molecule, and calculating at least one feature of the atomic structure and/or range of atomic structures using at least one calibration-free property of the diffraction pattern.

In one embodiment of the invention, the diffraction pattern is an electron diffraction pattern.

In one embodiment of the invention, the diffraction pattern is obtained from a sample of at least one tubular crystalline molecule using a transmission electron microscope.

In one embodiment of the invention, the at least one tubular crystalline molecule comprises a nanotube.

In one embodiment of the invention, the at least one molecule is a carbon nanotube and/or a carbon nanobud.

In one embodiment of the invention, the crystal structure and/or crystal orientation of the tubular crystalline molecule is uniquely specified by at least two mathematically independent parameters.

In one embodiment of the invention, the mathematical parameters uniquely specifying the nanotube or nanobud based molecule are chiral indices.

In one embodiment of the invention, the calibration-free property of the diffraction pattern is the pseudo-periodicity of the diffraction intensity along a layer line and/or the distance between at least two pairs of layer lines and/or the distance between the first pair of minima in the diffraction intensity along a layer line and/or the distance between the first pair of maxima in the diffraction intensity along a layer line and/or the area under the layer line intensity curve, and/or, the inner limit of the diffraction layer cloud, and/or the out limit of the diffraction layer cloud and/or the inner limit of the gap in the diffraction layer cloud and/or the outer limit of the gap in the diffraction layer cloud.

In one embodiment of the invention, the at least one calibration-free property is non-dimensionalized by dividing by at least one non-equivalent calibration-free property.

In one embodiment of the invention, the chiral indices are determined by simultaneously solving at least two coupled equations which relate at least two non-dimensionalized calibration-free properties to the non-tilt-corrected chiral indices.

In one embodiment of the invention, the at least two calibration-free properties to be non-dimensionalized are the distances between non-equatorial layer lines and the equatorial layer line and the non-dimensionalizing calibration-free property is the pseudo-periodicity of the diffraction intensity along the equatorial layer line.

In one embodiment of the invention, the non-tilt-corrected chiral indices are determined by simultaneously solving at least two coupled algebraic equations which relate the tilt-corrected chiral indices to the order of at least two Bessel functions corresponding to the vertices of at least two hexagons indexed based on a honeycomb lattice structure of the wall of the tubular crystalline molecule.

In one embodiment of the invention, the order of each Bessel function describing the variation in intensity of a signal from a given layer line is determined from at least one non-dimensionalized calibration-free property.

In one embodiment of the invention, the calibration-free property to be non-dimensionalized is the distance between the first pair of maxima in the diffraction intensity along at least one non-equatorial layer line and the non-dimensionalizing calibration-free property is the pseudo-periodicity of the diffraction intensity along the same layer line.

In one embodiment of the invention, the non-tilt-corrected chiral indices are tilt-corrected.

In one embodiment of the invention, the tilt-correction is achieved by truncating the non-tilt-corrected chiral indices to the nearest lower integer.

In one embodiment of the invention, the upper or lower limit of the chiral angle in a bundle of crystalline tubular molecules is determined by non-dimensionalizing the inner limit of the diffraction layer cloud and/or the inner limit of the gap in the diffraction layer cloud by the outer limit of the diffraction layer cloud and/or the outer limit of the gap in the diffraction layer cloud and solving an equation relating the non-dimensionalized inner limit to the molecule's chiral angle to determine the maximum and/or minimum chiral angle present in the bundle.

Furthermore, the inventive idea includes a computer program for determining the atomic structure of at least one tubular crystalline molecule, which computer program is further adapted to perform the above mentioned method steps, when executed on a data-processing device.

Furthermore, the inventive idea includes a device for determining the atomic structure of at least one tubular crystalline molecule, which device comprises means for performing the above mentioned method steps.

The presented method according to the invention allows the direct determination of (n, m) chiral indices of SWCNTs from their EDPs. Uniquely, the method is absolutely calibration-free and errors in structure determination due to the tubular crystalline molecule inclination with respect to the incident beam are specified. The tilt angle of the carbon tubular crystalline molecule with respect to the incident electron beam can be simultaneously evaluated, thus the effect of the tube inclination can be compensated for in the determination of the structure. In addition, several independent procedures are proposed to cross-check the results based on the new perceptions of the diffraction pattern.

The current invention, for the first time, allows the structure of tubular crystalline molecules to be unambiguously determined, and thus provides a means to exactly characterize the material. This is of enormous importance for both the scientific study and commercial application of such molecules in materials, components and devices.

DETAILED DESCRIPTION OF THE INVENTION

Figure 1:
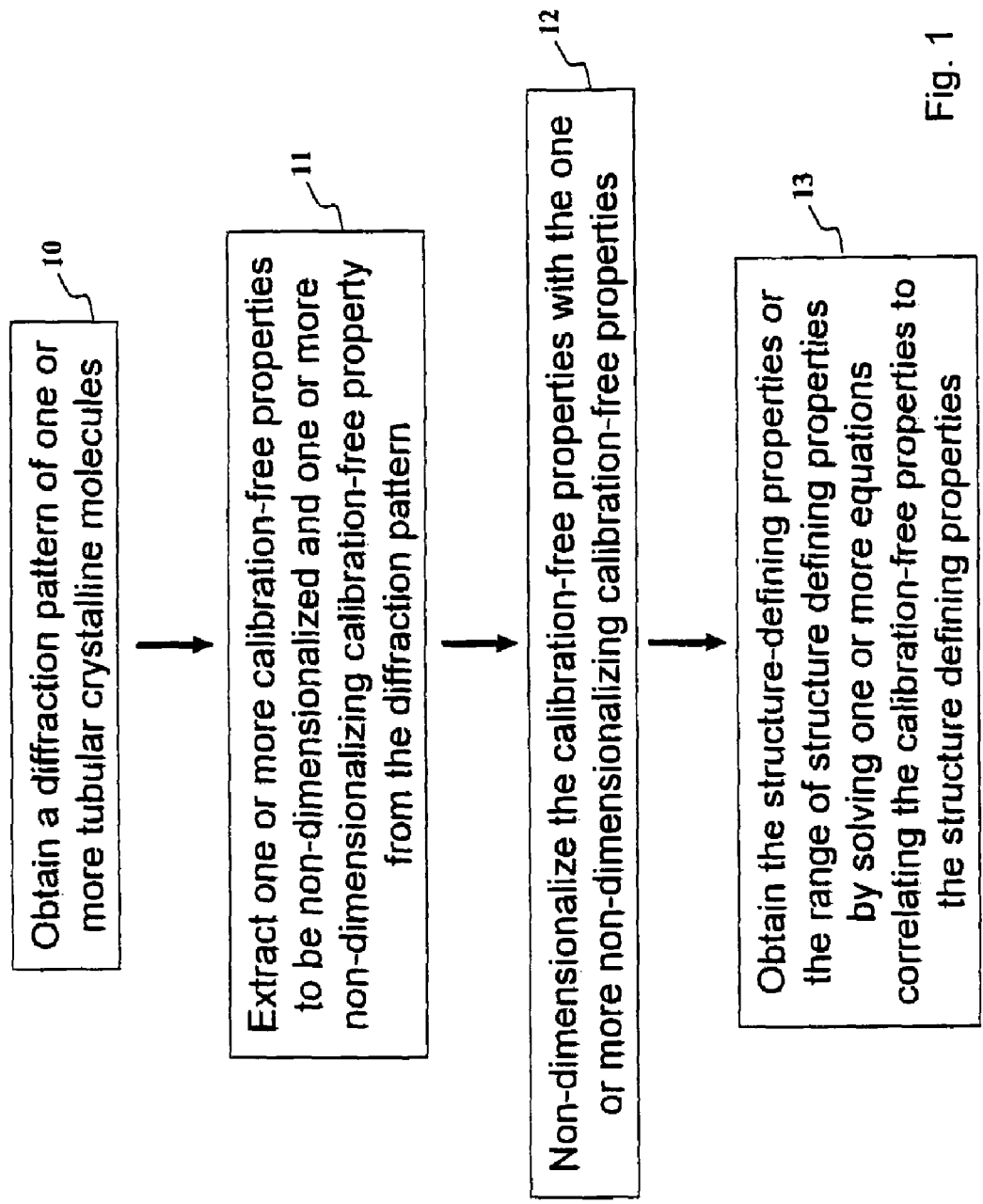
FIG. 1 shows a block diagram of the method for tubular crystalline molecule characterization.

The method for determining the atomic structure of one or more tubular crystalline molecules is presented in FIG. 1. First, a diffraction pattern of one or more tubular crystalline molecules is obtained 10. Next one or more calibration-free properties, together with one or more non-dimensionalizing calibration-free properties are measured from the diffraction pattern 11. Next, the calibration-free properties are non-dimensionalized with the one or more non-dimensionalizing calibration-free properties 12. Finally, the structure-defining properties or the range of structure defining properties are obtained by solving one or more equations correlating the calibration-free properties to the structure defining properties 13.

Figure 2:
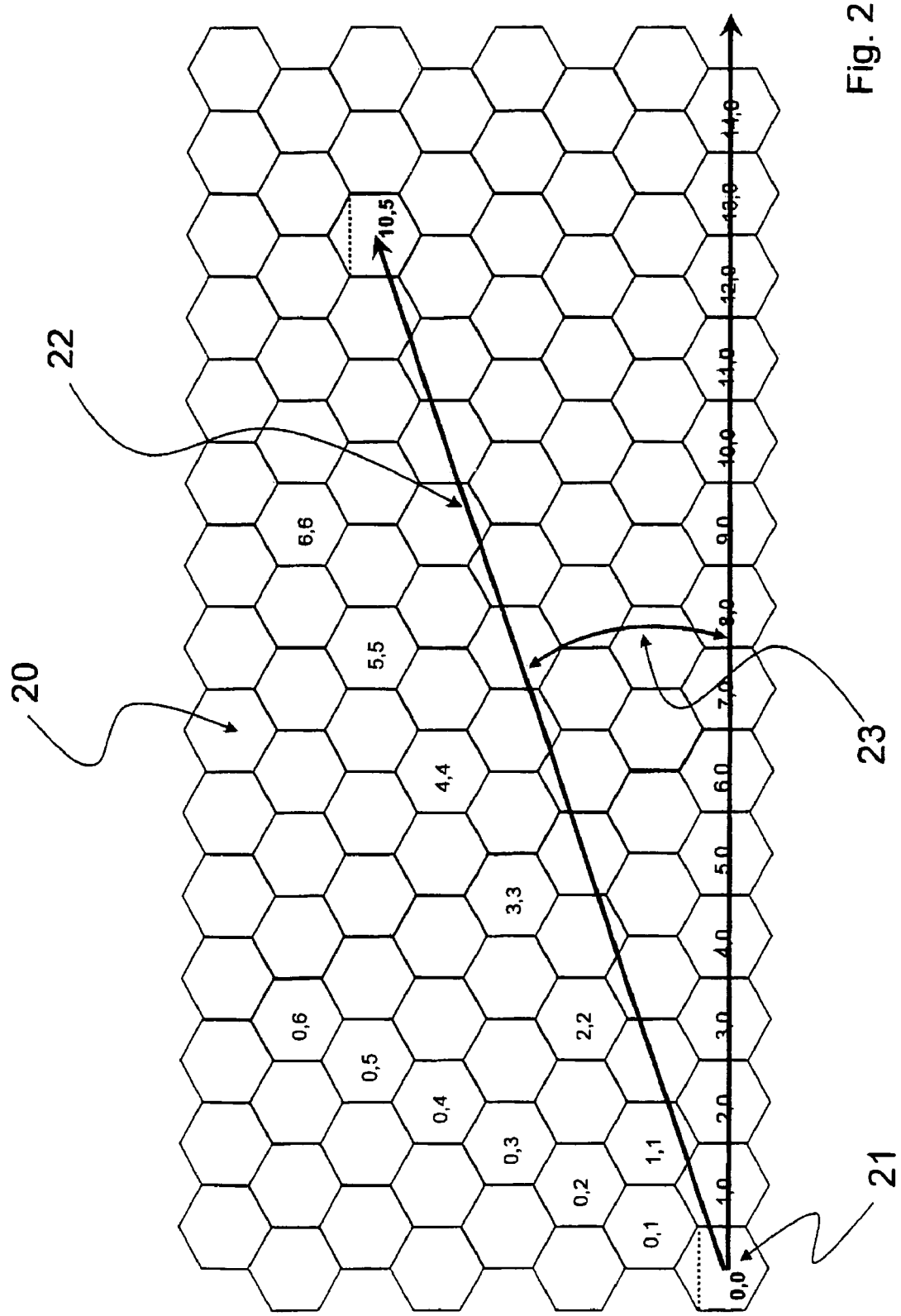
FIG. 2 shows the relationship between the chiral indices and the tube diameter and chiral angle in a carbon Nanotube which depicts a graphene sheet where each hexagon represents a ring of six carbon atoms.

The invention is described for determining the chirality of one or more single-walled carbon Nanotubes as an example of a typical tubular crystalline molecule, but the method is easily applicable to any molecule which can be uniquely defined by one or more independent parameters. For carbon Nanotubes, these are the chiral indices, or equivalently, the diameter and chiral angle. The relationship between the two is shown schematically in FIG. 2 which depicts a graphene sheet where each hexagon 20 represents a ring of six carbon atoms. The hexagons referenced from an origin (0,0) 21 have chiral indices (n, m). Each additional hexagon is indexed as shown in the FIG. 2. A particular carbon nanotube can then be represented by a particular chiral index in which the sheet is rolled such that the origin overlaps the given indexed hexagon. The diameter $D_o$ 22 and the chiral angle $\alpha$ 23 of the nanotube are thus specified which in the example of FIG. 2 are shown for chiral indices (n, m)=(10, 5).

Figure 3:
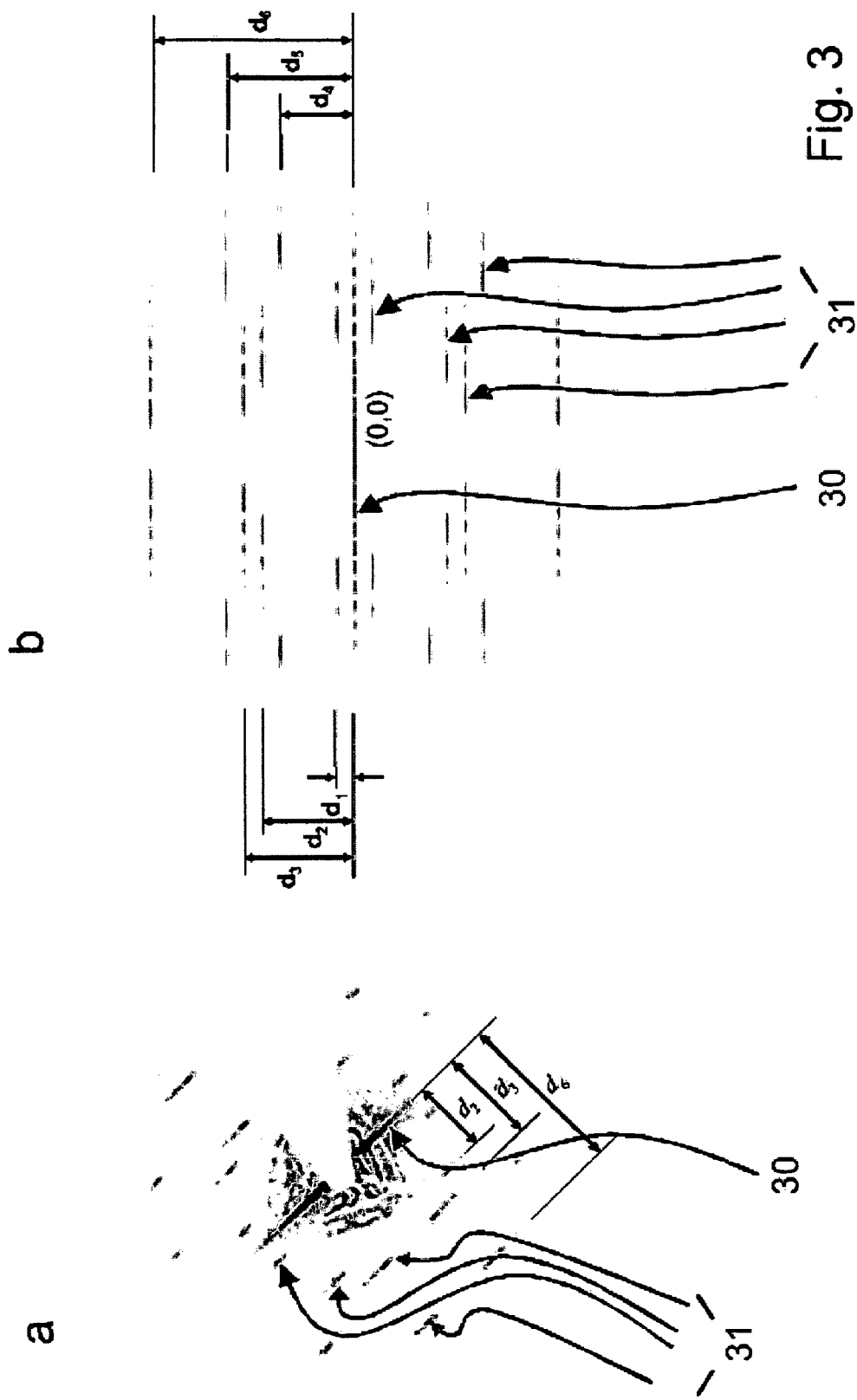
FIG. 3 shows typical measured and simulated diffraction patterns for a (23,10) single walled carbon nanotube.
Figure 4:
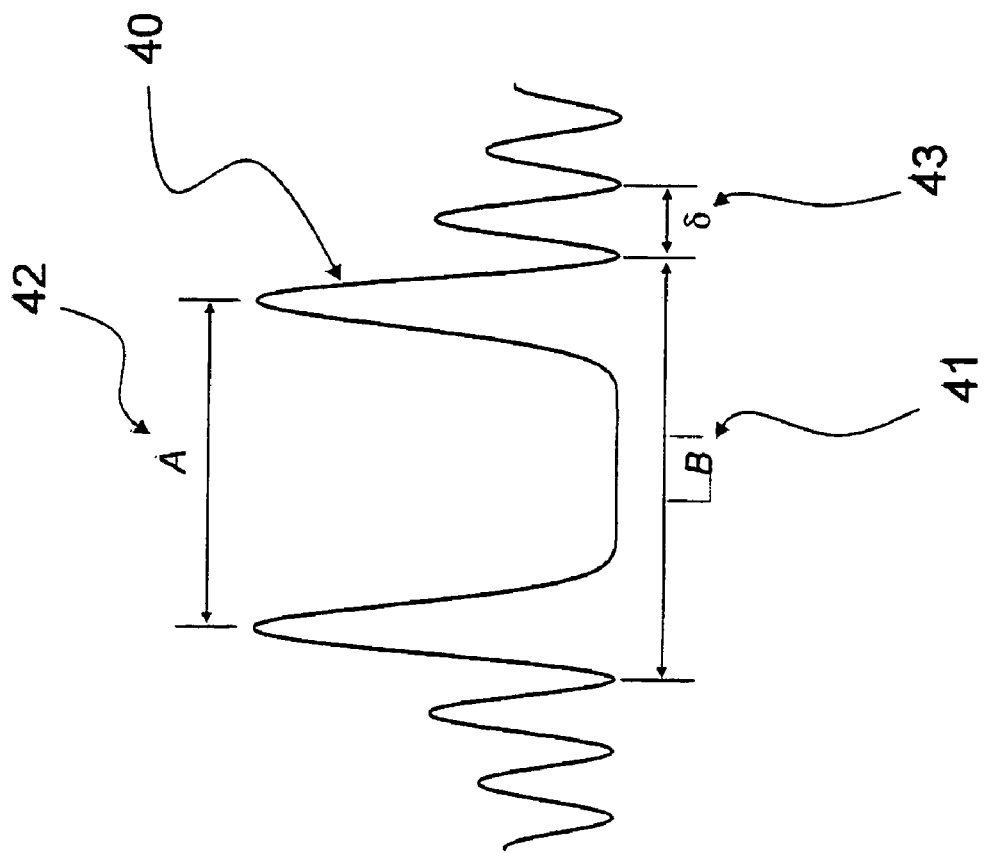
FIG. 4 shows additional independent calibration-free properties available from the intensity profile along a particular layer line, FIG. 5($a$) shows a measured EDP of a bundle of SWCNTs taken by a Philips CM200-FEG TEM with chiral angels clustered near 30 degrees, FIG. 5($b$) shows a simulated EDP of a bundle of SWCNTs with chiral angels clustered near zero, FIG. 6($a$) shows a simulated EDPs of a (12,7) SWCNT at a tilt angle of 5 degrees, FIG. 6($b$) shows a simulated EDPs of a (12,7) SWCNT at a tilt angle of 30 degrees, FIG. 7($a$) shows a simulated normal-incidence diffraction pattern of a chiral (25,2) single-walled carbon nanotube, FIG. 7($b$) shows the simulated intensity profile along the $L_2$ layer-line of a (25,2) single-walled carbon nanotube, FIG. 7($c$) shows the simulated intensity profile along the $L_3$ layer-line of a (25,2) single-walled carbon nanotube, FIG. 8($a$) shows a TEM measured diffraction pattern of a chiral (25,2) single-walled carbon nanotube, FIG. 8($b$) shows a TEM measured intensity profile along the $L_3$ layer-line of a single-walled carbon nanotube, and FIG. 8($c$) shows TEM measured intensity profile along the $L_6$ layer-line of a single-walled carbon nanotube.

In the method, at first, a diffraction pattern of one or more crystalline tubular molecules is obtained by, for instance, the use of a transmission electron microscope (TEM) or mathematical simulation. Typical measured and simulated diffraction patterns for single walled carbon nanotube are shown in FIGS. 3a and 3b where 30 is the equatorial layer line and 31 are non-equatorial layers lines. From such an image, one or more independent calibration-free properties can be measured which scale linearly when the image is scaled and so do not need to be calibrated with respect to each other. From the original diffraction pattern, the distance between pairs of layer lines satisfy this criterion. Shown are several layer line distances with respect to the equatorial layer line $d_1, d_2, d_3, d_4, d_5$ and $d_6$. Furthermore, as shown in FIG. 4, additional independent calibration-free properties are available from the intensity profile along any particular layer line 40. Each layer line represents a squared Bessel function of a particular order as will be explained in the examples. Independent calibration-free properties available from the intensity profile along any particular layer line i include, but are not limited to, $B_i$, the distance between the first pair of minima of the diffraction intensity along the layer line 41, $A_i$, the distance between the first pair of maxima in the diffraction intensity along a layer line 42, the pseudo-periodicity, $\delta_i$, of the diffraction intensity along a layer line 43 and the area under the layer line intensity curve. Other possible properties of the diffraction pattern according to the method and the above list do not, in any way, limit the scope of the invention. These constitute the possible calibration-free properties to be non-dimensionalized. Subsequently, a third and independent calibration-free property is chosen from the same list. This becomes the non-dimensionalizing calibration-free property. By dividing the calibration-free properties to be non-dimensionalized by the non-dimensionalizing calibration-free property, a set of one or more non-dimensionalized calibration-free properties is obtained. Importantly, these are independent of the scaling of the diffraction pattern and so need not be absolutely or independently calibrated, by, for instance, a measured reference distance such as a ruler or a chemical bond length. Subsequently, a set of equations is chosen which relates the non-dimensionalized calibration-free property to the properties to be determined which define the structure of the molecule. In the case of carbon Nanotubes, two chiral indices are required, or equivalently, the Nanotube diameter and the chiral angle and, consequently, two non-dimensionalized calibration-free properties are needed to uniquely define the nanotube. For other crystal structures, other parameters are possible and the preceding examples, in no way, limit the scope of the invention. Subsequently, the structure defining properties are determined by solving the coupled equations relating them to the non-dimensionalized calibration-free properties. A number of mathematical means for achieving this are possible according to the invention including, but not limited to, solving a system of algebraic equations or minimizing the error between ideal and measured diffraction patterns. This will be made clearer in the following examples.

In general, if the diffraction pattern is obtained from a molecule or a group of molecules not perpendicular to the incident beam generating the diffraction pattern, there will be an error in the calculated structure defining properties. The present invention allows this error to be corrected by truncation. This will be made clearer in the following examples where the method is applied to single walled carbon nanotubes to illustrate the execution of the method. This in no way limits the scope of the invention for other crystalline tubular molecules.

DETAILED DESCRIPTION OF A PREFERRED EMBODIMENT OF THE INVENTION

In the preferred embodiment of the method according to the invention, the two or more calibration-free properties to be non-dimensionalized are the distances between non-equatorial layer lines and the equatorial layer line and the non-dimensionalizing calibration-free property is the pseudo-periodicity of the diffraction intensity along the equatorial layer line.

FIG. 3a shows the EDP taken by a Philips CM200-FEG TEM operating at the highest possible accelerating voltage of 200 kV and a simulated EDP from a (23,10) SWCNT in a normal incidence. The microscope is equipped with a Gatan 794 multiscan CCD camera (1 k×1 k) for digital recording. The diffraction pattern is composed of many separate layer-lines parallel to each other but perpendicular to the tube axis. According to the kinematical diffraction theory of carbon nanotubes, the intensity profile along a certain layer-line is described by the sum of a series of squared Bessel functions. In particular, along the equatorial line 30 at the center, the dominant Bessel function is $J_0(\pi D_0 R)$, where R is the radial distance measured along the equatorial line from the diffraction center.

Mathematically, Bessel functions have an infinite number of minima (alternately termed zeros or roots) pseudo-periodically spaced. In practice, when $x=\pi D_0 R \gg 0$, the zeroth-order Bessel function $J_0(\pi D_0 R)$ or simply $J_0(x)$, can be approximated by $$J_0(x) = \sqrt{\frac{2}{\pi x}} \cos\left(x - \frac{\pi}{4}\right),$$

of which the roots are given by $$x_j = \pi D_0 R_j = \left(j - \frac{1}{4}\right)\pi,$$

where j is an integer greater than 1, and the interval between the neighboring roots is $x_{j+1} - x_j = \pi$. By this approximation we have then:

$$D_0 \cdot \delta_0 = 1, \text{ where } \delta_0 = R_{j+1} - R_j \quad (1)$$

It is worth remarking that the intensity profile on the equatorial line is totally independent of tube tilting, and thus so is the measurement of the value $\delta_0$.

The spacing $d_i$ (FIG. 1) of each non-equatorial layer-line measured from the equatorial line is subject to scaling by a tilt factor $$\frac{1}{\cos\tau},$$

where $\tau$ represents the tilt angle of the nanotube with $\tau=0°$ in the normal incidence condition. $d_i$ of the three layer-lines for the first-order hexagons are assigned $d_1, d_2, d_3$; and $d_4, d_5, d_6$ for the second-order hexagons.

Now by introducing a new term, the intrinsic layer-line spacing ($\xi_i$), which corresponds to each non-equatorial layer-line, is defined by:

$$\xi_i = D_0 \cdot d_i \qquad (2)$$

By geometrical considerations, expressions for $\xi_i$ of the six most important layer-lines corresponding to $d_i$ ($i=1, 2, \ldots, 6$) can be derived as $$\xi_1 = \frac{n-m}{\sqrt{3}\pi}, \xi_2 = \frac{n+2m}{\sqrt{3}\pi}, \xi_3 = \frac{2n+m}{\sqrt{3}\pi}, \qquad (3)$$

$$\xi_4 = \frac{\sqrt{3}m}{\pi}, \xi_5 = \frac{\sqrt{3}n}{\pi}, \xi_6 = \frac{\sqrt{3}(n+m)}{\pi}.$$

For example, since $$D_0 = \frac{\sqrt{n^2+m^2+nm}}{\pi} \cdot a,$$

$$d_3 = \frac{1}{d_{010}} \cdot \cos\alpha,$$

where $$d_{010} = \frac{\sqrt{3}}{2}a, \text{ and } \cos\alpha = \frac{2n+m}{2\sqrt{n^2+m^2+nm}},$$

we have $$\xi_3 = D_0 \cdot d_3 = \frac{2n+m}{\sqrt{3}\pi}.$$

Parameter $\alpha$ is the graphite lattice constant.

$\xi_i$ are nondimensional parameters and they are functions of only the chiral indices (n, m). On the other hand, $\xi_i$ can be readily measured from the diffraction pattern by $$\xi_i = \frac{d_i}{\delta}$$

if Eq. (1) and Eq. (2) are combined. It is obvious that the measured values of the intrinsic layer-line spacings ($\xi_i^\tau$) are scaled by $$\frac{1}{\cos\tau}.$$

The simultaneous solution of any two expressions of $\xi_i$ from Eq. (3) will give chiral indices (n, m). For instance, the solution of n and m from $\xi_2$ and $\xi_3$ is:

$$n = \frac{\pi}{\sqrt{3}} \cdot (2\xi_3 - \xi_2), \qquad (4)$$

-continued $$m = \frac{\pi}{\sqrt{3}} \cdot (2\xi_2 - \xi_3)$$

Or equivalently from $\xi_3$ and $\xi_6$, we have $$n = \frac{\pi}{\sqrt{3}} \cdot (3\xi_3 - \xi_6), \qquad (5)$$

$$m = \frac{\pi}{\sqrt{3}} \cdot (2\xi_6 - 3\xi_3)$$

In this way, the structure defining properties (the chiral indices) are determined by solving an algebraic system of equations relating them to the non-dimensionalized calibration-free properties of the diffraction pattern ($\xi_2$ and $\xi_3$ or $\xi_3$ and $\xi_6$) which are two pairs of distances between the non-equatorial layer lines and the equatorial layer line ($d_2$ and $d_3$ or $d_3$ and $d_6$) that are non-dimensionalized by $\delta$, the pseudo-periodicity of the equatorial layer line. Other combinations are possible according to the invention.

In more general cases, when the tilt angle $\tau$ is non-zero, the actual measured results ($n^\tau, m^\tau$) are given by:

$$n^\tau = n \cdot \frac{1}{\cos\tau} = n + \varepsilon_n, m^\tau = m \cdot \frac{1}{\cos\tau} = m + \varepsilon_m \qquad (6)$$

where $\epsilon_n$ and $\epsilon_m$ are tilt-effect errors, which are positive numbers. It is calculated that $\epsilon_i < 2$ ($i=n$ or m) for nanotubes with n or m being approximately at value 30 at a tilt angle of $\tau=20°$. When the tilt angle is small, so that $0 \leq \epsilon_i < 1$, then:

$$n = \text{TRUNC}(n^\tau) \text{ or } m = \text{TRUNC}(m^\tau); \qquad (7)$$

when the tilt angle becomes relatively large, so that $1 \leq \epsilon_i < 2$, then:

$$n = \text{TRUNC}(n^\tau) - 1 \text{ or } m = \text{TRUNC}(m^\tau) - 1. \qquad (8)$$

Here, TRUNC is a function to truncate a number into an integer by removing the fractional part of that number.

After (n, m) is determined, the tilt angle $\tau$ can be calculated from Eq. (6) by $$\cos\tau = \frac{n}{n^\tau} \text{ or } \cos\tau = \frac{m}{m^\tau}.$$

Since the intrinsic layer-line spacings $\xi_i$ are more sensitive to the tube tilting, the tilt angle is more robustly evaluated by $$\cos\tau = \frac{\xi_i}{\xi_i^\tau},$$

for instance, $$\cos\tau = \frac{\xi_3}{\xi_3^\tau} \qquad (9)$$

-continued $$= \frac{2n+m}{\sqrt{3}\pi \cdot \xi_3^\tau}$$

$$= \frac{\xi_6}{\xi_6^\tau}$$

$$= \frac{\sqrt{3}(n+m)}{\pi \cdot \xi_6^\tau}$$

With the tilt angle $\tau$ taken into account, the absolute calibration of the diffraction pattern can be carried out a posteriori by any of the layer-line spacings $d_i$, for example, $$d_3 = \frac{2\sqrt{3}}{3a} \cdot \frac{\cos\alpha}{\cos\tau} \quad (10)$$

Here, the graphite lattice constant $\alpha$ is known to be 0.246 nm.

The major sources of error in the method arise from the intrinsic measurement errors of $\delta_0 = R_{j+1} - R_j$ and $d_i$, especially the relatively small magnitude of $\delta$ as a divisor to calculate the intrinsic layer-line spacing $\xi_i^\tau$.

Another error source arises when the tilt angle is large so that there is no confident criterion in practice to make a correct selection between Eq. (7) or Eq. (8) to determine (n, m). In order to stay in the range where Eq. (7) is valid (i.e. so as not to invoke Eq. (8)), we introduce the tolerated tilt angle $\tau^{max}$ for nanotubes of different (n, m). Theoretically $\tau^{max}$ for a certain n can be estimated by $$\cos(\tau^{max}) = \lim_{\varepsilon^{max} \to 1^-} \left(\frac{n}{n+\varepsilon^{max}}\right).$$

As the integer n increases, the tolerated tilt angle $\tau^{max}$ decreases. For instance, supposing $\epsilon^{max} = 0.9$, the tolerated tilt angle is allowed to be as large as 20° for n=15. In addition, based on Eq. (6), an intrinsic index ratio $\beta$, which is a function of (n, m), is introduced where $$\beta = \frac{m}{n} = \frac{m+\varepsilon_m}{n+\varepsilon_n} = \frac{\varepsilon_m}{\varepsilon_n} \leq 1,$$

hence $\epsilon_m \leq \epsilon_n$. It can be seen that the method allows equal or higher tilt angle to be tolerated when determining m (compared to n). In other words, it is favorable to first calculate m based on Eq. (7). n can then be more reliably derived by applying the intrinsic index ratio $\beta$, since $\beta$ can be tilt-independently measured by $$\beta = \frac{m}{n} = \frac{2\xi_2 - \xi_3}{2\xi_3 - \xi_2}$$

according to Eq. (4); or by $$\beta = \frac{m}{n} = \frac{2\xi_6 - 3\xi_3}{3\xi_3 - \xi_6}$$

according to Eq. (5).

By this procedure, in general situations when the tilt angle is not larger than 20°, SWCNTs with chiral indices (n, m) ($n \geq 15 \geq m$) can be directly measured without ambiguity by using Eq. (7) to first derive m. As before, n can be calculated by using the parameter $\beta$. If m or n is incorrectly determined due to, for example, pixelation errors, the mistake should be recognized easily from the resultant unreasonable tilt angle; or the results can be cross-checked by the n measurement based on Eq. (7) or Eq. (8). For example, from FIG. 2a ($\tau=5°$), if m is incorrectly determined to be 6, n then should be 10 by applying the parameter $\beta$. The resultant tilt angle is then approximately 33°, which is too large to be a normal case. On the other hand, if n is incorrectly calculated to be 11, while m is correctly determined to be 7, this will signal a serious mismatch of the intrinsic ratio $\beta$ between the measured value from $\xi_i^\tau$ and the calculated value by $$\frac{m}{n}.$$

Determination of the tube diameter $D_0$ after calibration of the EDP based on Eq. (10) can also be independently employed to verify the results. Of course, the results can further be cross-checked by measuring different layer-lines separately. When the tilt angle is beyond the tolerated limit, in addition to the above-mentioned cross-checking procedure, a trial-and-error procedure around all adjacent (n, m) candidates can be applied.

It is worth noting that this method is also applicable for (n, m) determination of achiral nanotubes (i.e., armchair and zigzag tubes), with $d_1 = 0$, $d_2 = d_3 = d_4 = d_5$, $d_6 = 2d_2$ for an armchair nanotube; and $d_1 = d_2$, $d_3 = 2d_1$, $d_4 = 0$, $d5 = d_6 = 3d_1$ for a zigzag tube.

Since only the layer-line spacings $d_i$ and the interval $\delta_0$ between the zeros along the equatorial line are involved in the measurement, the present method has no significant limitations. In contrast, the method has a high degree of flexibility and verifiability in that (n, m) can be determined by using many combinations of layer-line spacings. One important remark is that the EDP is required to resolve the zeros on the equatorial line so that $\delta_0$ can be measured with confidence.

Description of an Alternate Embodiment

In the present alternate embodiment of the method, the chiral indices are determined by simultaneously solving two or more coupled algebraic equations which relate the tilt-corrected chiral indices to the order of two or more Bessel functions corresponding to the vertices of two or more hexagons indexed based on the honeycomb lattice structure of the wall of the tubular crystalline molecule. Here the calibration-free properties are first used to define the order of each Bessel function describing the variation in intensity of the signal from a given layer line. The calibration-free property to be non-dimensionalized is the distance between the first pair of maxima in the diffraction intensity along one or more non-equatorial layer lines and the non-dimensionalizing calibration-free property is the pseudo-periodicity of the diffraction intensity along the same layer line. Other combinations and choices of calibration-free properties to be non-dimensionalized and non-dimensionalizing calibration-free properties are possible according to the invention.

The chiral indices (n, m) of a SWCNT are correlated with the orders of Bessel functions (squared) that act as shape factors for the diffraction from the nanotube. This enables direct evaluation of the chiral indices of carbon nanotubes. Unambiguous determination of (n, m) then depends on reliably retrieving the Bessel orders from the corresponding Bessel functions. Bessel factors have a mirror symmetry about x=0. For a Bessel factor having a non-zero order, there is always an "intensity-gap" around x=0, where the intensity is approaching zero. The width of the gap is also a function of the Bessel factor order. A higher order Bessel factor has a wider intensity-gap than a lower order Bessel factor. On the other hand, the interval between the first two positive roots $\delta_i$ of a Bessel factor increases much more slowly with the absolute value of the Bessel order $|v|$. Therefore, non-dimensional characteristic ratios for each individual Bessel factor can be calculated by dividing $A_i$ or $B_i$ by $\delta_i$ as:

$$R_{A_i} = \frac{A_i}{\delta_i} \tag{11}$$

or $$R_{B_i} = \frac{B_i}{\delta_i} \tag{12}$$

As examples, for Bessel factors of orders $v=9$ and $v=10$, $R_{Ai}$ is 5.51 and 5.95 respectively, with an absolute difference of 0.44. Likewise, $R_{Bi}$ is 6.87 and 7.31, also with a difference of 0.44. The corresponding differential precision for distinguishing these two Bessel factors is then 7.9% when using $R_{Ai}$, or 6.2% when using $R_{Bi}$. In the case of Bessel factors of higher orders $v=29$ and $v=30$, the absolute differences of their $R_{Ai}$ ratios and of their $R_{Bi}$ ratios are both as large as 0.31, with differential precisions being 2.4% and 2.2%, respectively. Therefore, the introduction of $R_{Ai}$ and $R_{Bi}$ allows much higher differential precisions for distinguishing adjacent Bessel factors, thus allowing the use of layer-lines dominated by high-order Bessel functions. Bessel function, which is associated with (n, m) by:

$$v = nh - mk, \tag{13}$$

Characteristic ratios $R_{Ai}$ and $R_{Bi}$ for Bessel factors of orders from $v=0$ to 30 have been tabulated and listed in Table 1. By comparing the ratios measured from the intensity profiles along diffraction layer-lines with those listed in Table 1, Bessel orders can immediately be recognized, which are then ascribed to the chiral indices of the nanotube. By using several combinations of $R_{Ai}$ and $R_{Bi}$ from different layer-line measurements to complement and verify each other in a measurement, a high level of confidence can be achieved.

TABLE 1

Characteristic ratios $R_{Ai}$ and $R_{Bi}$ for Bessel factors of orders from $v = 0$ to 30.

| $|v|$ | $R_A$ | $R_B$ |
|---|---|---|
| 1 | 1.156 | 2.407 |
| 2 | 1.859 | 3.130 |
| 3 | 2.485 | 3.774 |
| 4 | 3.061 | 4.366 |
| 5 | 3.600 | 4.918 |
| 6 | 4.106 | 5.440 |
| 7 | 4.595 | 5.937 |
| 8 | 5.062 | 6.413 |
| 9 | 5.511 | 6.871 |
| 10 | 5.947 | 7.315 |
| 11 | 6.373 | 7.744 |
| 12 | 6.784 | 8.162 |
| 13 | 7.187 | 8.569 |
| 14 | 7.581 | 8.966 |
| 15 | 7.963 | 9.355 |
| 16 | 8.338 | 9.735 |
| 17 | 8.707 | 10.11 |
| 18 | 9.070 | 10.47 |
| 19 | 9.427 | 10.83 |
| 20 | 9.779 | 11.19 |
| 21 | 10.12 | 11.53 |
| 22 | 10.46 | 11.88 |
| 23 | 10.80 | 12.21 |
| 24 | 11.13 | 12.55 |
| 25 | 11.46 | 12.87 |
| 26 | 11.78 | 13.20 |
| 27 | 12.10 | 13.52 |
| 28 | 12.41 | 13.83 |
| 29 | 12.72 | 14.15 |
| 30 | 13.03 | 14.46 |

The method can be applied to determine range of chiral angles present in a bundle of SWCNTs. FIG. 5a shows a measured EDP of a bundle of SWCNTs taken by a Philips CM200-FEG TEM with chiral angels clustered near 30 degrees. The inner and outer limits ($d_{in}$ and $d_{out}$) of the diffraction layer cloud 50 correspond to the limits of the minimum chiral angle present in the bundle. By non-dimensionalizing $d_{in}$ by $d_{out}$ according to equation (14):

$$\tan\alpha = \frac{1}{\sqrt{3}}\left(2\frac{d_{in}}{d_{out}} - 1\right), \tag{14}$$

the minimum chiral angle in the bundle is determined. FIG. 5b shows a simulated EDP of a bundle of SWCNTs with chiral angels clustered near zero. Here the inner and outer limits ($d_{in}$ and $d_{out}$) of the gap in the diffraction layer cloud 51 correspond to the limits of the maximum chiral angle present in the bundle. By non-dimensionalizing $d_{in}$ by $d_{out}$ according to equation (14), the maximum chiral angle in the bundle can be determined.

Further Embodiments of the Invention

The method according to the invention is demonstrated on both simulated and experimental diffraction patterns of single-walled carbon nanotubes. The technique can be readily extended to structural analysis of nanotubes of other materials with structure analog to carbon nanotubes, such as boron nitride Nanotubes and carbon nanobuds.

EXAMPLE 1

Figure 6:
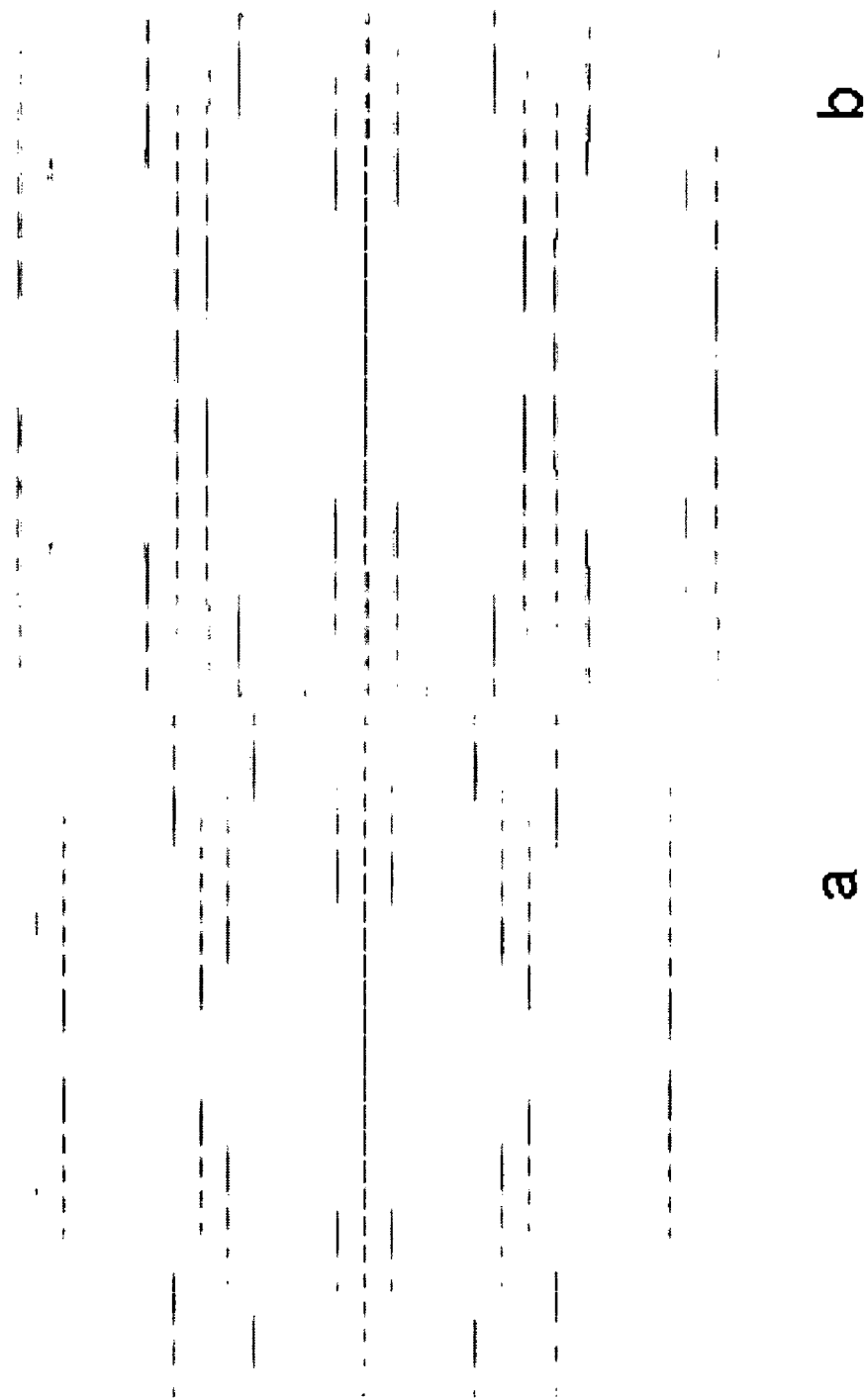

Material: (12,7) SWCNT
Diffraction pattern from: Simulation
Structure defining property: Chiral indices (n,m)
Calibration-free properties to be non-dimensionalized: $d_3$ and $d_6$
Non-dimensionalizing calibration-free property: $\delta$ In order to test the method, we simulate a tilt-series of EDPs of a (12,7) SWCNT. Two of them are shown in FIG. 6 at tilt angels of 5 and 30 degrees. By applying the ($\xi_3, \xi_6$) set of equations, chiral indices (n, m) and the tilt angles $\tau$ are determined as summarized in Table 2, in which $2\xi_i^\tau$ (i=3 or 6) are measured from the simulated patterns; $2\xi_i(n,m)$ are calculated from Eq. (3). The tilt angles, $\tau_i$ (i=3 or 6), are determined by using the intrinsic layer-line spacings based on Eq. (9).

It is clearly seen that, when the tilt angle is less than 20°, the chiral indices can be directly measured without ambiguity. The error for the case when the tilt is 5° (FIG. 2a) and $\epsilon_n = -0.02 < 0$ is due to the pixel resolution limitation, which can be avoided by improving the pixel resolution of the EDP. As the tilt angle increases as large as 25°, $\epsilon_n = 1.21 > 1$, while $\epsilon_m = 0.74 < 1$; when the tilt angle reaches 30°, both $\epsilon_n$ and $\epsilon_m$ become larger than 1. In such situations, one must be cautious when calculating (n, m) from Eq. (7) or Eq. (8). This will be discussed later in more detail.

TABLE 2

Determination of chiral indices, (n, m), and tilt angles, τ, from a tilt-series of simulated EDPs of a (12, 7) tube by measuring $d_3$ and $d_6$ layer-lines. The listed tilt angles, $\tau_i$ (i = 3, or 6) are calculated based on Eq. (9).

| (n, m) | Simulated tilt angles | $2\xi_3^\tau$ | $2\xi_3(12, 7)$ | $\tau_3$ | $2\xi_6^\tau$ | $2\xi_6(12, 7)$ | $\tau_6$ | $n^\tau$ | n | $\epsilon_n$ | $m^\tau$ | m | $\epsilon_m$ |
|---|---|---|---|---|---|---|---|---|---|---|---|---|---|
| (12, 7) | 0° | 11.413 | 11.394 | 3.30° | 20.979 | 20.950 | 3.01° | 12.03 | 12 | 0.03 | 7.00 | 7 | 0.00 |
| | 5° | 11.413 | | 3.30° | 21.033 | | 5.09° | 11.98 | (11 + 1) | −0.02$^a$ | 7.10 | 7 | 0.10 |
| | 10° | 11.549 | | 9.40° | 21.250 | | 9.64° | 12.15 | 12 | 0.15 | 7.12 | 7 | 0.12 |
| | 15° | 11.793 | | 14.93° | 21.685 | | 14.96° | 12.42 | 12 | 0.42 | 7.25 | 7 | 0.25 |
| | 20° | 12.120 | | 19.92° | 22.283 | | 19.92° | 12.77 | 12 | 0.77 | 7.44 | 7 | 0.44 |
| | 25° | 12.554 | | 24.83° | 23.098 | | 24.90° | 13.21 | (13 − 1) | 1.21 | 7.74 | 7 | 0.74 |
| | 30° | 13.152 | | 29.97° | 24.185 | | 29.98° | 13.85 | (13 − 1) | 1.85 | 8.08 | (8 − 1) | 1.08 |

$^a\epsilon_n < 0$ is due to the pixel resolution limitation (see the text).

EXAMPLE 2

Material: (12,7) SWCNT
Diffraction pattern from: TEM
Structure defining property: Chiral indices (n,m)
Calibration-free properties to be non-dimensionalized: $d_2$, $d_3$ and $d_6$
Non-dimensionalizing calibration-free property: δ

To apply the method to real problems, high-quality EDPs of individual SWCNTs are essential but in reality difficult to obtain because of their weak scattering power and the tendency for the tubes to be easily modified by the electron beam. FIG. 3a shows a high-resolution TEM image of an individual SWCNT. The $(\xi_2,\xi_3)$ set of equations and the $(\xi_3,\xi_6)$ set of equations are independently employed for the calculations with results summarized in Table 2 (a) and Table 2 (b), respectively. The chiral indices (n, m) of the SWCNT are thus determined to be (23, 10) and the tilt angle τ is determined to be approximately 10° from both equation sets.

With the tilt angle τ=10° taken into account, we can accurately calibrate the diffraction pattern by using, for instance, $$d_3 = \frac{2\sqrt{3}}{3a} \cdot \frac{\cos\alpha}{\cos\tau} 4.554 \text{ nm}^{-1};$$

hence the tube diameter is determined to be 2.29 nm from the EDP based on Eq. (1), which accurately matches the (23, 10) tube.

EXAMPLE 3

Material: (23,10) SWCNT
Diffraction pattern from: Simulation
Structure defining property: Chiral indices (n,m)
Calibration-free properties to be non-dimensionalized: $d_3$ and $d_6$
Non-dimensionalizing calibration-free property: δ

A simulated EDP of the (23, 10) nanotube at a tilt of 10° is presented in FIG. 3b, on which a similar measurement is performed. The corresponding results are also listed in Table 2 (a) and 2 (b) for comparison. Again, there is an excellent match between results from the simulated diffraction pattern and the experimental pattern.

EXAMPLE 4

Figure 7:
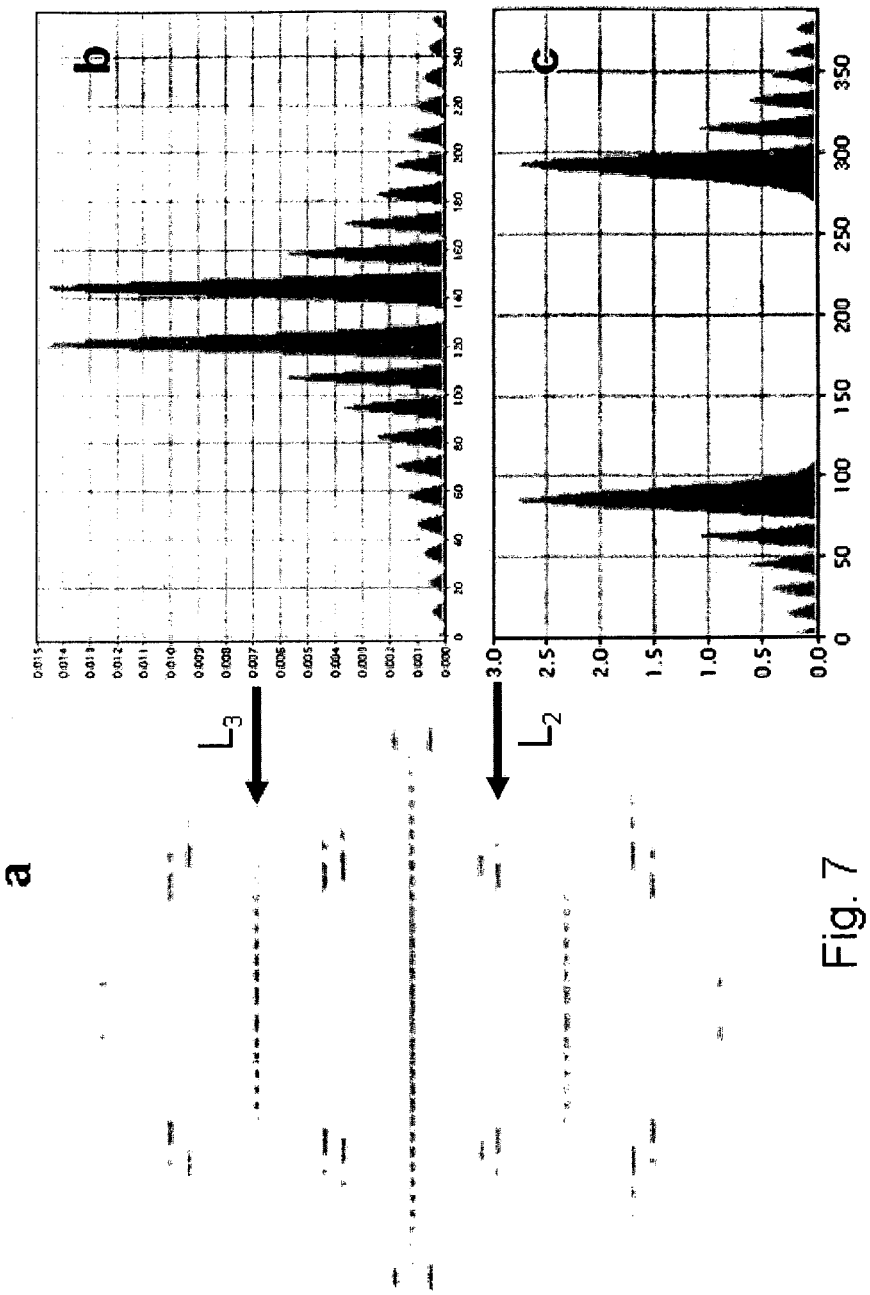

Material: (25,2) SWCNT
Diffraction pattern from: Simulation
Structure defining property: Chiral indices (n,m)
Calibration-free properties to be non-dimensionalized: $A_i$ and $B_i$
Non-dimensionalizing calibration-free property: $\delta_i$ As an example, FIG. 7a presents a simulated normal-incidence diffraction pattern of a chiral (25,2) single-walled carbon nanotube. FIGS. 7c and 7b show the corresponding intensity profiles along the $L_2$ and $L_3$ layer-lines. Table 3 lists the ratios $R_{Ai}$ and $R_{Bi}$ calculated from both the $L_2$ and $L_3$ layer-lines. By comparing with their nearest characteristic values in Table 1, the Bessel orders are directly recognizable as $v_n$=25 and $v_m$=2 accordingly for $L_2$ and $L_3$ layer-lines with little ambiguity.

TABLE 3

Ratios $R_{Ai}$ and $R_{Bi}$ determined from $L_2$ and $L_3$ layer-lines on the diffraction patterns of a (25, 2) nanotube, and the corresponding best fit values of the Bessel orders.

| | $L_2$ Layer-line | | $L_3$ Layer-line | |
|---|---|---|---|---|
| Ratios | Determined values | $v_n$ of the best fit | determined values | $v_m$ of the best fit |
| $R_{Ai}$ | 11.5 | 25 | 1.88 | 2 |
| $R_{Bi}$ | 13.0 | 25 | 3.20 | 2 |

EXAMPLE 5

Figure 8:
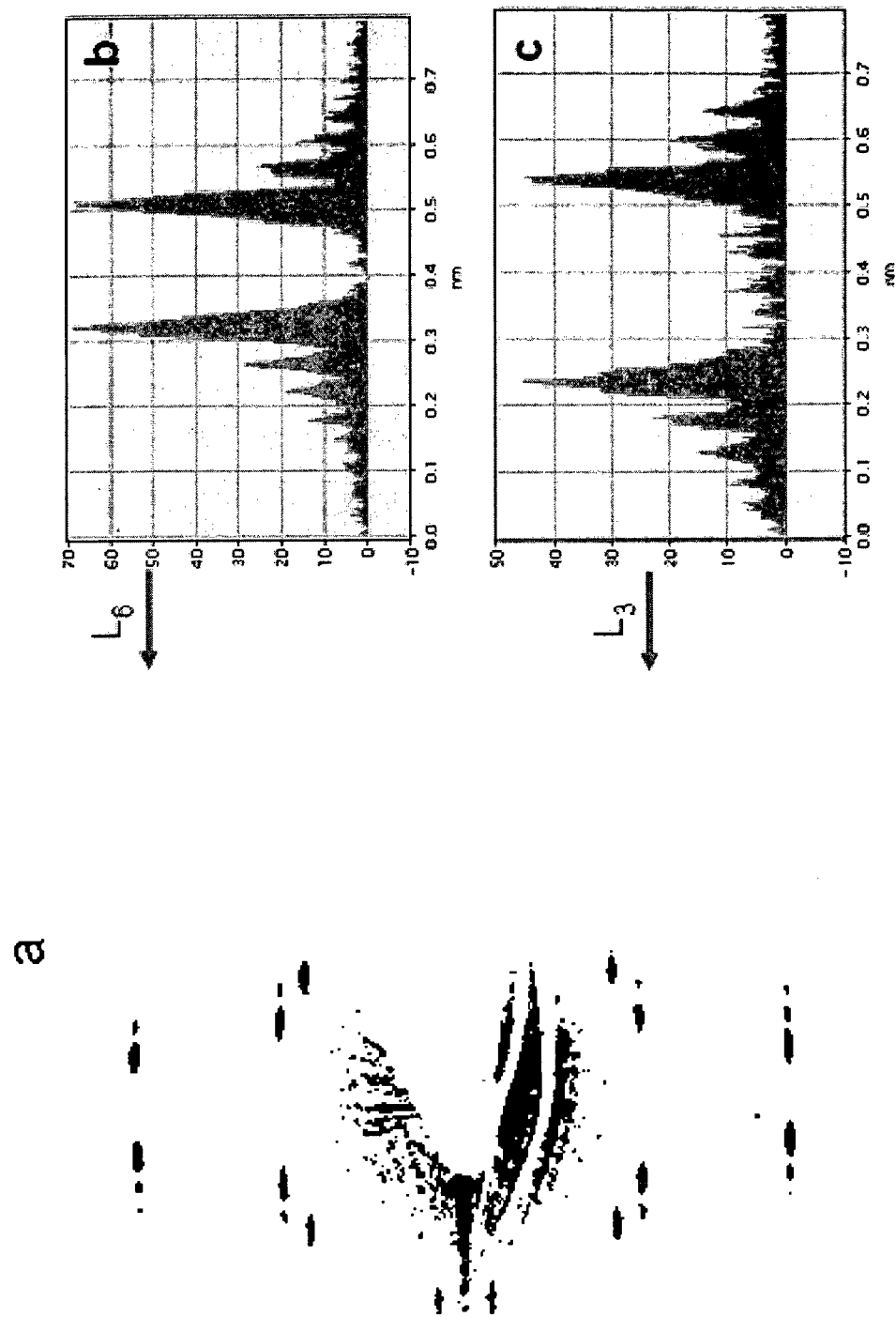

Material: (18,11) SWCNT
Diffraction pattern from: TEM
Structure defining property: Chiral indices (n,m)
Calibration-free properties to be non-dimensionalized: $A_i$ and $B_i$
Non-dimensionalizing calibration-free property: $\delta_i$ The proposed method has been applied to determine the chiral indices of real single-walled carbon nanotubes. FIG. 8a shows the EDP of an individual SWCNT taken by a Philips CM200-FEG TEM operating at the highest possible accelerating voltage of 200 kV. The microscope is equipped with a Gatan 794 multiscan CCD camera (1 k×1 k) for digital recording. The layer-lines passing through (0, 1) and (1, 1) reflections as labeled $L_3$ and $L_6$ in FIG. 8a are employed for (n, m) determination. The intensity profiles along $L_3$ and $L_6$ layer-lines are shown in FIGS. 8 (c) and (b), respectively. From $L_3$ layer-line, $R_{Ai}$ is calculated to be 6.53, based on which the chiral index m is confidently identified as 11. Likewise, from $L_6$ layer-line $R_{Ai}$ is calculated to be 4.0, giving the value n−m=7, thus n is recognized to be 18. This (23, 10) tube is a semiconducting nanotube of diameter $D_0$=2.29 nm, and chiral angle α=17.2°.

TABLE 4

Ratios and determined from $L_3$ and $L_6$ layer-lines on the diffraction patterns of a (25, 2) nanotube, and the corresponding best fit values of the Bessel orders.

| Ratios | $L_3$ Layer-line | | $L_6$ Layer-line | |
|---|---|---|---|---|
| | Determined values | $v_m$ of the best fit | determined values | $v_{n-m}$ of the best fit |
| $R_{Ai}$ | 4.0 | 11 | 4.4 | 7 |
| $R_{Bi}$ | 5.5 | 11 | 6.1 | 7 |

EXAMPLE 6

Material: Bundle of SWCNTs having a high chiral angle
Diffraction pattern from: TEM
Structure defining property: Minimum chiral angle (α) in the bundle
Calibration-free properties to be non-dimensionalized: $d_{in}$
Non-dimensionalizing calibration-free properties: $d_{out}$ The proposed method is applied to determine range of chiral angles present in a bundle of SWCNTs. FIG. 5a shows a measured EDP of a bundle of SWCNTs with chiral angels clustered near 30 degrees. The inner and outer limits ($d_{in}$ and $d_{out}$) of the diffraction layer cloud correspond to the limits of the minimum chiral angle present in the bundle. By non-dimensionalizing $d_{in}$ by $d_{out}$ according to equation (14), the minimum chiral angle in the bundle is determined to be 23.9 degrees.

EXAMPLE 7

Material: Bundle of SWCNTs having a low chiral angle
Diffraction pattern from: Simulation
Structure defining property: Maximum chiral angle (α) in the bundle
Calibration-free properties to be non-dimensionalized: $d_{in}$
Non-dimensionalizing calibration-free properties: $d_{out}$ FIG. 5b shows a simulated EDP of a bundle of SWCNTs with chiral angles clustered near zero. Here the inner and outer limits ($d_{in}$ and $d_{out}$) of the gap in the diffraction layer cloud correspond to the limits of the maximum chiral angle present in the bundle. By non-dimensionalizing $d_{in}$ by $d_{out}$ according to equation (14), the maximum chiral angle in the bundle is determined to be 13.9 degrees.

It is obvious to a person skilled in the art that with the advancement of technology, the basic idea of the invention may be implemented in various ways. The invention and its embodiments are thus not limited to the examples described above; instead they may vary within the scope of the claims.

The invention claimed is:

1. A method for determining the atomic structure of at least one tubular crystalline molecule, wherein the method comprises the following steps:
obtaining an electron diffraction pattern of at least one tubular crystalline molecule;
calculating at least one feature of the atomic structure and/or range of atomic structures using at least one calibration-free property of the electron diffraction pattern; and
compensating for an effect of an unexpected, unknown or otherwise uncontrolled tilt angle of the tubular crystalline molecule with respect to an electron beam.

2. The method according to claim 1, wherein the diffraction pattern is obtained from a sample of at least one tubular crystalline molecule using a transmission electron microscope.

3. The method according to claim 1, wherein the at least one tubular crystalline molecule comprises a nanotube.

4. The method according to claim 1, wherein the at least one molecule is a carbon nanotube and/or a carbon nanobud.

5. The method according to claim 1, wherein the crystal structure and/or crystal orientation of the tubular crystalline molecule is uniquely specified by at least two mathematically independent parameters.

6. The method according to claim 5, wherein the mathematical parameters uniquely specifying the nanotube or nanobud based molecule are chiral indices.

7. The method according to claim 1, wherein the calibration-free property of the diffraction pattern is the pseudo-periodicity of the diffraction intensity along a layer line and/or the distance between at least two pairs of layer lines and/or the distance between the first pair of minima in the diffraction intensity along a layer line and/or the distance between the first pair of maxima in the diffraction intensity along a layer line and/or the area under the layer line intensity curve, and/or, the inner limit of a diffraction layer cloud, and/or the out limit of the diffraction layer cloud and/or the inner limit of the gap in the diffraction layer cloud and/or the outer limit of the gap in the diffraction layer cloud.

8. The method according to claim 1, wherein the at least one calibration-free property is non-dimensionalized by dividing by at least one non-equivalent calibration-free property.

9. The method according to claim 6, wherein the chiral indices are determined by simultaneously solving at least two coupled equations which relate at least two non-dimensionalized calibration-free properties to a non-tilt-corrected chiral indices.

10. The method according to claim 8, wherein at least two calibration-free properties to be non-dimensionalized are the distances between non-equatorial layer lines and the equatorial layer line and the non-dimensionalizing calibration-free property is the pseudo-periodicity of the diffraction intensity along the equatorial layer line.

11. The method according to claim 9, wherein the non-tilt-corrected chiral indices are determined by simultaneously solving at least two coupled algebraic equations which relate the tilt-corrected chiral indices to the order of at least two Bessel functions corresponding to the vertices of at least two hexagons indexed based on a honeycomb lattice structure of the wall of the tubular crystalline molecule.

12. The method according to claim 8, wherein the order of each Bessel function describing the variation in intensity of a signal from a given layer line is determined from at least one non-dimensionalized calibration-free property.

13. The method according to claim 8, wherein the calibration-free property to be non-dimensionalized is the distance between the first pair of maxima in the diffraction intensity along at least one non-equatorial layer line and the non-dimensionalizing calibration-free property is the pseudo-periodicity of the diffraction intensity along the same layer line.

14. The method according to claim 1, wherein a non-tilt-corrected chiral indices are tilt-corrected.

15. The method according to claim 1, wherein a tilt-correction is achieved by truncating a non-tilt-corrected chiral indices to the nearest lower integer.

16. The method according to claim 1, wherein the upper or lower limit of a chiral angle in a bundle of crystalline tubular molecules is determined by non-dimensionalizing the inner limit of a diffraction layer cloud and/or the inner limit of the gap in the diffraction layer cloud by the outer limit of the diffraction layer cloud and/or the outer limit of the gap in the diffraction layer cloud and solving an equation relating the non-dimensionalized inner limit to the molecule's chiral angle to determine the maximum and/or minimum chiral angle present in the bundle.

17. A computer readable medium comprising a computer program for determining the atomic structure of at least one tubular crystalline molecule, wherein the computer program is adapted to perform the following steps when executed on a data-processing device:

obtaining an electron diffraction pattern of at least one tubular crystalline molecule;

calculating at least one feature of the atomic structure and/or range of atomic structures using at least one calibration-free property of the electron diffraction pattern; and compensating for an effect of an unexpected, unknown or otherwise uncontrolled tilt angle of the tubular crystalline molecule with respect to an electron beam.

18. A device for determining the atomic structure of at least one tubular crystalline molecule, wherein the device comprises:

a means for obtaining an electron diffraction pattern of at least one tubular crystalline molecule;

a means for calculating at least one feature of the atomic structure and/or range of atomic structures using at least one calibration-free property of the electron diffraction pattern; and compensating for an effect of an unexpected, unknown or otherwise uncontrolled tilt angle of the tubular crystalline molecule with respect to an electron beam.

19. The method according to claim 1, wherein the at least one tubular crystalline molecule comprises a nanotube.

\* \* \* \* \*